United States Patent [19]

Toth

[11] 4,012,426

[45] Mar. 15, 1977

[54] PURIFICATION OF 1-NITROANTHRAQUINONE

[75] Inventor: Istvan Toth, Bottmingen, Switzerland

[73] Assignee: Sandoz Ltd., Basel, Switzerland

[22] Filed: Jan. 29, 1973

[21] Appl. No.: 327,621

[30] Foreign Application Priority Data

Feb. 1, 1972 Switzerland .................. 1499/72
Feb. 15, 1972 Switzerland .................. 2180/72
Aug. 22, 1972 Switzerland .................. 12403/72

[52] U.S. Cl. .................................. 260/369
[51] Int. Cl. .................................. C09d 1/00
[58] Field of Search .................................. 260/369

[56] References Cited

UNITED STATES PATENTS 2,302,729  11/1942  Whelen .................. 260/369
3,766,222  10/1973  Hartwig et al. .................. 260/369

FOREIGN PATENTS OR APPLICATIONS 2,206,960  8/1972  Germany .................. 260/369

*Primary Examiner*—Jane S. Myers
*Attorney, Agent, or Firm*—Gerald D. Sharkin; Richard E. Vila; Thomas C. Doyle

[57] ABSTRACT

This invention provides a purification process for crude 1-nitroanthraquinone which comprises treating the crude 1-nitroanthraquinone with a base or a basic hydrolyzable salt, in the presence of a solvent and at an elevated temperature, and isolating the purified 1-nitroanthraquinone. The process particularly removes substantial proportions of dinitroanthraquinones and oxidation products.

13 Claims, No Drawings

PURIFICATION OF 1-NITROANTHRAQUINONE

The present invention relates to a purification process for 1-nitro-anthraquinones.

In the nitration of anthraquinones for the production of 1-nitroanthraquinone more or less substantial amounts of by-products are formed, in particular dinitroanthraquinones, notably 1,5- and 1,8-dinitroanthraquinones, along with oxidation products such as ocyanthraquinones and oxynitroanthraquinones. These by-products are invariably formed, whether the nitration of anthraquinones is carried out with nitric acid in the presence of sulphuric acid, with nitric acid in the presence of phosphoric acid, or with nitric acid alone. By a judicious choice of the nitration medium and the nitrating conditions, the amount of dinitroanthraquinone can be significantly reduced; at a very low degree of nitration, for example, the amount of dinitroanthraquinones relative to 1-nitroanthraquinone can be cut down to about 3 to 4%, while at higher degrees of nitration, for example 95%, the amount of dinitroanthraquinones relative to 1-nitroanthraquinone can be reduced to about 7%.

It has now been found that the nitroanthraquinone thus produced can be substantially freed from the dinitroanthraquinones, i.e,. that the amount of the latter relative to the 1-nitroanthraquinone may be reduced to less than 1.5% or even less than 1% or 0.5%, by treatment of the nitration product with a base or with a salt hydrolysable to a base. Utilizing the different solubilities, the 1-nitroanthraquinone can then be separated from the salts of the anthraquinone compounds containing OH groups and from the reaction products of the dinitroanthraquinones.

The present invention provides a process for the purification of crude 1-nitroanthraquinone which comprises treating the crude 1-nitroanthraquinone with a base or a basic hydrolysable salt, in the presence of a solvent and at a temperature above room temperature, and isolating the purified 1-nitroanthraquinone.

The bases suitable for use in the process are suitably, for example, inorganic bases, in particular alkali-metal hydroxides such as lithium hydroxide, sodium hydroxide and potassium hydroxide, alkaline-earth metal hydroxides and/or oxides such as magnesium, calcium, strontium and barium hydroxide and/or oxide. Basic hydrolysable salts are salts which reach a hydrolytic equilibrium in water according to the following equation:

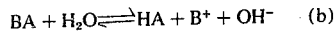

$$BA + H_2O \rightleftharpoons HA + B^+ + OH^-  \quad (b)$$

(B is a cation and A an anion); the acid HA also is partly ionized according to the equation:

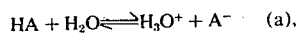

$$HA + H_2O \rightleftharpoons H_3O^+ + A^-  \quad (a),$$

but ionization as in (b) is preponderant over the ionization as in (a). For the present invention basic hydrolyzable salts in which the PKa value of equation (a) is at least 3 are preferred.

Examples of HA acids suitable for forming basic hydrolysable salts are carbonic acid, monhydrogen phosphates, nitrous acid, boric acid, carboxylic acids, e.g., formic, acetic, oxalic, benzoic acid; hydroxycarboxylic acids, e.g., ascorbic, citric, salicylic acid; acid reacting hydroxyaryl compounds, e.g., phenol, p-nitrophenol, uric acid; weaker sulphonic acids, e.g., aminophenylsulphonic acids. Examples of basic hydrolysable salts are the alkali-metal salts of the aforenamed acids, in particular the lithium, sodium and potassium salts, and the basic salts of alkaline-earth metals, e.g., magnesium, calcium, strontium and barium.

The base can be employed in the stoichiometric amount or in great excess; the stoichiometric amount is understood to be the quantity sufficient for reaction of the anthraquinone derivatives which are present in crude nitroanthraquinone along with 1-nitroanthraquinone.

Preferably alkali metal hydroxides are used for the process of this invention, optionally together with the corresponding carbonates.

The suitable solvents include those which are miscible with water and those which have low miscibility or are non-miscible with water, and in which preferably nitroanthraquinone is well soluble and which are stable to the base or salt and nitroanthraquinone under the reaction conditions, provided they are not themselves used as reactants. Examples of suitable solvents which are non-miscible or poorly miscible with water are aliphatic and/or aromatic halogenated hydrocarbons, e.g., chlorobenzene, dichlorobenzene, chlorinated alkanes, especially 1,2-dichlorethane; nitrobenzene; ethers, e.g., anisol, phenethol, dioxan; and secondary and tertiary amines, e.g., methyl aniline, dimethyl, dimethyl aniline. Examples of solvents well miscible with water are alcohols, e.g., ethanol, cyclohexanol, benzyl alcohol; glycols, e.g., ethylene glycol; ketones, e.g., acetone, acetyl acetone; amides, e.g., dimethyl formamide, dimethyl acetamide, hexamethyl phosphoramide; dimethyl sulphoxide; phenols, e.g., cresol; water-soluble secondary and tertiary amines, e.g., trimethyl amine and N-methyl pyrrolidone. Under suitable conditions water itself can be used as solvent, preferably in mixture with other solvents. The said solvents can generally be employed alone or in admixture with each other (as solutions or emulsions). The crude nitroanthraquinone for purification may be present as a pure, more or less concentrated solution or as a suspension in the selected solvent or solvent mixture.

It is generally of advantage to proceed by dissolving the crude nitroanthraquinone in a suitable solvent and treating it at above room temperature with a base, after which the 1-nitroanthraquinone is separated from the anthraquinone compounds of different solubility. It is of advantage for example, to work so that the 1-nitroanthraquinone remains in solution while the reaction products of the dinitroanthraquinone and the hydroxy derivatives of the anthraquinone and the nitroanthraquinone settle out at the reaction temperature or after cooling and/or concentration by evaporation. After the liquid and solid phases have been separated, the 1-nitroanthraquinone can be isolated from the solution by one of the known methods.

A suitable procedure comprises dissolving the crude nitroanthraquinone in a solvent which is not miscible with water and treating it above room temperature with a base dissolved in water or in a water-miscible solvent (this solution being preferably as highly concentrated as possible), so that the 1-nitroanthraquinone remains in solution in the organic non-water-miscible solvent while the reaction products of the hydroxy derivatives of the anthraquinone and the nitroanthraquinone and the dinitroanthraquinones, which are not soluble in the said solvent, are either precipitated or go partially or wholly into solution in the water or the water-miscible solvent. The purified 1-nitroanthraquinone present in dissolved form can then be isolated by separating the liquid from the solid and/or second liquid phase, with subsequent precipitation, evaporation, or the two solvents can be used in such amounts that an azeotropic solvent mixture can be distilled while the solvent in which only the 1-nitroanthraquinone is dissolved is replaced so that at the end of distillation the undissolved compounds can be separated from the solution of the 1-nitroanthraquinone. When this procedure is employed, an aqueous alkaline solution of at least 40%, preferably at least 50% strength, can be used as second solvent.

A further suitable operating procedure comprises dissolving the crude nitroanthraquinone in a water-miscible solvent, treating it with the base and separating the product with a second solvent. It is also possible to work with a mixture of a non-water-miscible solvent and water-miscible solvent and to separate the 1-nitroanthraquinone from the by-products during distillation by azeotropic distillation of the mixture and replacement of one of the two solvents, preferably the solvent not miscible with water.

The process temperature is advantageously chosen with regard to the nature and amount of the solvent or solvents and the concentration and amount of the base, the temperature being preferably one at which the 1-nitroanthraquinone is completely dissolved in the solvent, and is compatible with the reaction. It is of advantage to work at temperatures between 40° C and the boiling point of the reaction mixture, if necessary under pressure, though it is preferably not to exceed 200° C. The preferred temperature range is usually 50° to 150° C.

A further mode of operation of the present process comprises preliminary purification of the crude nitroanthraquinone in a suitable solvent followed by treatment with the base in the same solvent. It is expedient to employ a solvent in which the solubility of the 1-nitroanthraquinone is markedly different from the solubility of the dinitroanthraquinones. The crude nitroanthraquinone is treated with sufficient solvent and at temperatures at which all the 1-nitroanthraquinone present goes into solution; the undissolved (and reprecipitated or recrystallized) proportions are separated from the solution by mechanical means and the solution treated further with the base. This procedure is specially suitable for working up nitroanthraquinone mixtures with a high content of dinitroanthraquinones notably 1,5- and 1,8-dinitroanthraquinone. In this way a practically pure α,α'-dinitroanthraquinone mixture can be obtained, as over-nitration leads predominantly to the formation of α,α'-dinitroanthraquinones which are the less soluble components of the crude nitroanthraquinone mixture.

In general the crude 1-nitroanthraquinone, which is contaminated by dinitroanthraquinone may be produced from anthraquinone by any of the known nitration methods, for example by nitration of anthraquinone in the presence of sulphuric acid or phosphoric acid or by nitration of anthraquinone with concentrated nitric acid alone; the last-named method can be carried out, for example, at −40° C to the boiling point of the reaction medium and in the presence of a great excess of nitric acid of at least 90% strength. The nitration product can be submitted to the process of this invention as obtained after separation and washing, for example as a moist or dry filtercake, or if desired after intermediate purification.

In the following illustrative Examples, the parts and percentages, unless otherwise stated, are by weight and the temperatures in degrees centigrade; the parts by weight relate to the parts by volume as grams to cubic centimeters. The nitroanthraquinone mixtures used as starting products contain on the average 0.5 to 5% nitrohydroxyanthraquinones.

EXAMPLE 1

150 Parts of a nitroanthraquinone paste with a 47.5% dry content of the composition given below are suspended in 1500 parts by volume of 1,2-dichlorethane. The mixture is raised to the boiling temperature (at 73° the azeotropic water/1,2-dichlorethane mixture distils) and at this temperature 40 parts by volume of 50% potassium hydroxide solution are added dropwise in about 5 to 10 minutes with thorough stirring. Distillation is continued until the temperature of the reaction mixture rises to 79°–80° while the distilled 1,2dichlorethane is continuously replaced so that the total volume remains constant. As soon as the internal temperature reaches 80° one part of activated carbon is stirred into the reaction mixture. The reaction mixture is then filtered and washed with 100 parts by volume of warm 1,2-dichlorethane. The mother lye is concentrated by evaporation.

Analysis of the nitration products

Starting product:
 anthraquinone: 0.72%
 2-nitroanthraquinone: 0.2%
 1-nitroanthraquinone: 91.7%
 1,5-dinitroanthraquinone: 4.35%
 1,8-dinitroanthraquinone: 2.45%
Final Product:
 anthraquinone: 1.20%
 2-nitroanthraquinone: 0.3%
 1-nitroanthraquinone: 97.3%
 1,5-dinitroanthraquinone: 0.3%
 1,8-dinitroanthraquinone: 0%

EXAMPLE 2

150 Parts of a nitroanthraquinone paste with 47.5% dry content of the composition given below under (a) (starting product) are suspended in 1800 parts by volume of 1,2-dichlorethane. The suspension is raised to the boiling temperature (at 73° the azeotropic water/1,2-dichlorethane mixture distils) and 21 parts of 50% potassium hydroxide solution are added at this temperature in 5minutes with vigorous stirring. The azeotropic mixture is distilled for 1 hour, during which time the internal temperature increases to 83°–84°, while the 1,2-dichlorethane removed by distillation is continuously replaced so that the total volume remains constant. As soon as the internal temperature reaches 84° 3 parts of activated carbon are added, then stirring is continued and if necessary 2 parts of calcium dichloride are added. The suspension is cooled to 75° and filtered. The filter residue is washed with 200 parts by volume of 1,2-dichlorethane at 80°. After concentration of the filtrate in a rotary evaporator 63 parts of 97–98% nitroanthraquinone are obtained, which contains no further dinitro products and agrees with the composition of the final product specified under (a) below.

If a starting product of the composition (b) given below is used in this Example in place of one of the composition (a), a final product corresponding to the composition given under (b) is obtained.

| Analysis of the nitration products | | starting product | | final product | |
|---|---|---|---|---|---|
| a) | anthraquinone | 0.72 | % | 1.15 | % |
| | 2-nitroanthraquinone | 0.2 | % | 0.29 | % |
| | 1-nitroanthraquinone | 91.7 | % | 97.7 | % |
| | 1,5-dinitroanthraquinone | 4.35 | % | 0 | % |
| | 1,8-dinitroanthraquinone | 2.45 | % | 0 | % |
| b) | anthraquinone | 0.56 | % | 0.63 | % |
| | 2-nitroanthraquinone | 0.13 | % | 0.13 | % |
| | 1-nitroanthraquinone | 90.83 | % | 98.94 | % |
| | 1,5-dinitroanthraquinone | 3.0 | % | 0 | % |
| | 1,8-dinitroanthraquinone | 0.48 | % | 0 | % |
| | 2,7-dinitroanthraquinone | 0.11 | % | 0 | % |
| | nitrohydroxyanthraquinones | 4.0 | % | 0 | % |

EXAMPLE 3

70 Parts of a nitroanthraquinone mixture containing approximately 92% 1-nitroanthraquinone and approximately 4–5% dinitroanthraquinone are mixed as an aqueous paste with 560 parts of anisole to form a homogeneous suspension. The suspension is heated to 115° and the evaporating water separated in a separator, on which the solid particles go into solution. With stirring, 12 parts of sodium hydroxide in powder form are entered into the solution at 115°. The mixture is stirred further at the same temperature for 2 hours and then filtered. The filtrate is evaporated to precipitate the 1-nitroanthraquinone, which is filtered free from the mother lye, washed and dried. The 1-nitroanthraquinone thus obtained is of about 98% purity and contains approximately 0.3% dinitroanthraquinone. The yield is 93–95% of theory.

EXAMPLE 4

25 Parts of nitroanthraquinone with a content of about 58% 1-nitroanthraquinone and about 37% dinitroanthraquinone are dissolved in 250 parts of dimethyl formamide at 150°. Subsequently 0.5 parts of sodium nitrite are added. After reaction for 30 minutes the solution is evaporated to one-sixth of the initial volume and cooled. The crystalline product is filtered, washed and dried. The product is obtained in a yield of 10.4 parts and contains approximately 90% nitroanthraquinone and about 4% dinitroanthraquinone.

EXAMPLE 5

25 Parts of nitroanthraquinone with a content of about 58% 1-nitroanthraquinone and about 37% dinitroanthraquinone are dissolved in 250 parts of dimethyl formamide at 150°. At this temperature the solution is allowed to react with 5 parts of magnesium oxide for 23 hours. Subsequently it is filtered, the filtrate evaporated to one sixth of the initial volume and cooled; the crystalline product is then separated and dried. The yield of the product is 9 parts and it contains approximately 95% 1-nitroanthraquinone and about 1% dinitroanthraquinone.

EXAMPLE 6

22.7 Parts of a nitroanthraquinone paste of 63% dry content (containing 70% 1-nitroanthraquinone, the remaining 30% being mainly dinitroanthraquinone) are suspended in 227 parts of 1,2-dichlorethane, with the subsequent addition of 10 parts of sodium hydroxide. The mixture is heated to the distillation temperature, at which the azeotropic water/1,2-dichlorethane mixture is distilled. Distillation is continued until the temperature of the reaction mixture has increased to 83°, the 1,2-dichlorethane removed by distillation being continuously replaced so that the volume remains constant throughout. The reaction mixture is then filtered and washed with 25 parts by volume of 1,2-dichlorethane. The mother lye is evaporated. The yield is 9.5 parts of 95–98% 1-nitroanthraquinone.

EXAMPLE 7

(Preliminary purification of crude nitroanthraquinone)

100 Parts of crude nitroanthraquinone containing 60% 1-nitroanthraquinone, 6% 1,5-dinitroanthraquinone, 13% 1,8-dinitroanthraquinone and 20% β,β'-dinitroanthraquinones are stirred into 1000 parts of anisole. The solution is raised to 115° and stirred further for 1 hour at this temperature. Without cooling it is filtered at 115°. The filter residue consists of 7 parts of a dinitroanthraquinone mixture. The filtrate is worked up as described in Example 3 to isolate the 1-nitroanthraquinone.

What is claimed is:

1. A process for the purification of crude 1-nitroanthraquinone containing an impurity comprising dinitroanthraquinone which process comprises treating said crude 1-nitroanthraquinone with an alkali metal hydroxide or alkaline earth metal oxide or hydroxide or with an alkali metal or alkaline earth metal salt of an acid or acid reacting compound selected from the group consisting of carbonic acid, monohydrogen phosphates, nitrous acid, boric acid, formic acid, acetic acid, benzoic acid, ascorbic acid, citric acid, salicylic acid, phenol, p-nitrophenol, uric acid and aminophenylsulphonic acids at a temperature above room temperature and in the presence of a first solvent which is stable under the reaction conditions and in which the 1-nitroanthraquinone is soluble at the treatment temperature, whereby said impurity forms a reaction product whose solubility in said first solvent is different to that of the 1-nitroanthraquinone, separating the dissolved 1-nitroanthraquinone from the reaction product and recovering the purified 1-nitroanthraquinone from said first solvent, the base or basic hydrolysable salt being employed in an amount at least sufficient to react with said impurity.

2. A process according to claim 1, in which a mixture of a water-miscible solvent and a water-immiscible solvent is used.

3. A process according to claim 2, in which the purified 1-nitroanthraquinone is isolated by azeotropic distillation of the solvent mixture.

4. A process according to claim 1, in which the process is carried out at from 40° C to the boiling temperature of the reaction mixture.

5. A process according to claim 4, in which the temperature is from 50° to 150° C.

6. A process according to claim 4, wherein the reaction product is caused to settle out of the solution of 1-nitroanthraquinone in the first solvent.

7. A process according to claim 1, wherein the solubility of the reaction product in the first solvent is less than that of the 1-nitroanthraquinone.

8. A process according to claim 7, wherein the crude 1-nitroanthraquinone is treated with an alkali metal hydroxide.

9. A process according to claim 7, in which the base or salt is used in the form of a solution of at least 40% in a second solvent which is water or a water-miscible liquid, and the first solvent is water immiscible whereby the reaction product precipitates or goes into solution in the second solvent while the 1-nitroanthraquinone remains in solution in the first solvent.

10. A process according to claim 9, in which the solution of base or salt in the second solvent is of a concentration of at least 50% by weight.

11. A process according to claim 7, in which the crude 1-nitroanthraquinone is dissolved in a water-miscible solvent, treated with the base or salt and the reaction product is extracted with a further solvent.

12. A process according to claim 7, in which the crude 1-nitroanthraquinone is subjected to a preliminary purification by a suitable solvent whereby the 1-nitroanthraquinone is dissolved in said suitable solvent and the impurities of different solubility are removed, and the resulting partially purified solution of 1-nitroanthraquinone is then treated with the base or basic hydrolysable salt.

13. A process for the purification of crude 1-nitroanthraquinone containing an impurity comprising dinitroanthraquinone which process comprises treating said crude 1-nitroanthraquinone with an alkali metal or alkaline earth metal salt of phenol or p-nitrophenol at a temperature above room temperature and in the presence of a solvent which is stable under the reaction conditions and in which the 1-nitroanthraquinone is soluble at the treatment temperature, whereby said impurity forms a reaction product whose solubility in said solvent is different from that of the 1-nitroanthraquinone, separating the 1-nitroanthraquinone from the reaction product and recovering the purified 1-nitroanthraquinone, said salt being employed in an amount at least sufficient to react with said impurity.

* * * * *